United States Patent
Hancu et al.

(10) Patent No.: US 10,878,561 B2
(45) Date of Patent: Dec. 29, 2020

(54) AUTOMATED SCANNING WORKFLOW

(71) Applicant: General Electric Company, Schenectady, NY (US)

(72) Inventors: Ileana Hancu, Clifton Park, NY (US); Thomas Kwok-Fah Foo, Clifton Park, NY (US); Desmond Teck-Beng Yeo, Albany, NY (US); Arathi Sreekumari, Bangalore (IN); Dattesh Dayanand Shanbhag, Bangalore (IN); Dirk Wim Jos Beque, Munich (DE)

(73) Assignee: General Electric Company, Schenectady, NY (US)

( * ) Notice: Subject to any disclaimer, the term of this patent is extended or adjusted under 35 U.S.C. 154(b) by 239 days.

(21) Appl. No.: 15/994,925

(22) Filed: May 31, 2018

(65) Prior Publication Data

US 2019/0370958 A1  Dec. 5, 2019

(51) Int. Cl.
*G06K 9/00* (2006.01)
*G06T 7/00* (2017.01)
*G16H 50/20* (2018.01)
*G16H 10/60* (2018.01)
*G16H 30/20* (2018.01)

(52) U.S. Cl.
CPC .......... *G06T 7/0012* (2013.01); *G16H 10/60* (2018.01); *G16H 30/20* (2018.01); *G16H 50/20* (2018.01); *G06T 2207/10088* (2013.01)

(58) Field of Classification Search
CPC ........ G06T 7/0012; G06T 2207/10088; G16H 30/20; G16H 10/60; G16H 50/20; G16H 30/40

USPC ......................................................... 382/128
See application file for complete search history.

(56) References Cited

U.S. PATENT DOCUMENTS

| | | | |
|---|---|---|---|
| 8,520,920 B2 | 8/2013 | Guehring et al. | |
| 8,988,074 B2 | 3/2015 | Oliveira et al. | |
| 9,568,578 B2* | 2/2017 | Senegas | G01R 33/543 |
| 2011/0210734 A1* | 9/2011 | Darrow | G06K 9/6284 |
| | | | 324/309 |
| 2013/0090946 A1* | 4/2013 | Foo | G16H 30/20 |
| | | | 705/3 |

(Continued)

OTHER PUBLICATIONS

Mortamet, Benedicte, et al.; "Automatic quality assessment in structural brain magnetic resonance imaging", Magnetic Resonance in Medicine, vol. 62, Issue: 2, pp. 365-372, Jun. 12, 2009.

(Continued)

*Primary Examiner* — Van D Huynh

(57) ABSTRACT

The present disclosure provides, in certain implementations, a rule-based or deep learning-based approach capable of assessing diagnostic utility of images in near real time with respect to acquisition. Correspondingly, an automated implementation of such an algorithm on the scanner would, in fact, emulate the doctor himself rating images in real time, and reduce the number of unneeded re-scans and recalls. In one aspect of the present invention it was found that diagnostic utility of an image is not an absolute measure, but instead depends upon the reading radiologist and the scan indication (i.e., the purpose of the scan). Therefore, adapting the threshold (probability of an imaging volume to be deemed good) as a function of reading radiologist and scan indication can result in decreasing the number of re-scans and recalls.

20 Claims, 5 Drawing Sheets

(56) References Cited

U.S. PATENT DOCUMENTS

2017/0156630 A1* 6/2017 Gabr .................... A61B 5/0037
2017/0185713 A1   6/2017 Bhatia et al.
2017/0337329 A1  11/2017 Liu et al.
2019/0228547 A1*  7/2019 Chandarana ......... G06N 3/0481

OTHER PUBLICATIONS

Grimes, Joshua, et al.; "Implementation and evaluation of a protocol management system for automated review of CT protocols", Journal of Applied Clinical Medical Physics, vol. 17, Issue: 5, pp. 523-533, Sep. 8, 2016.

* cited by examiner

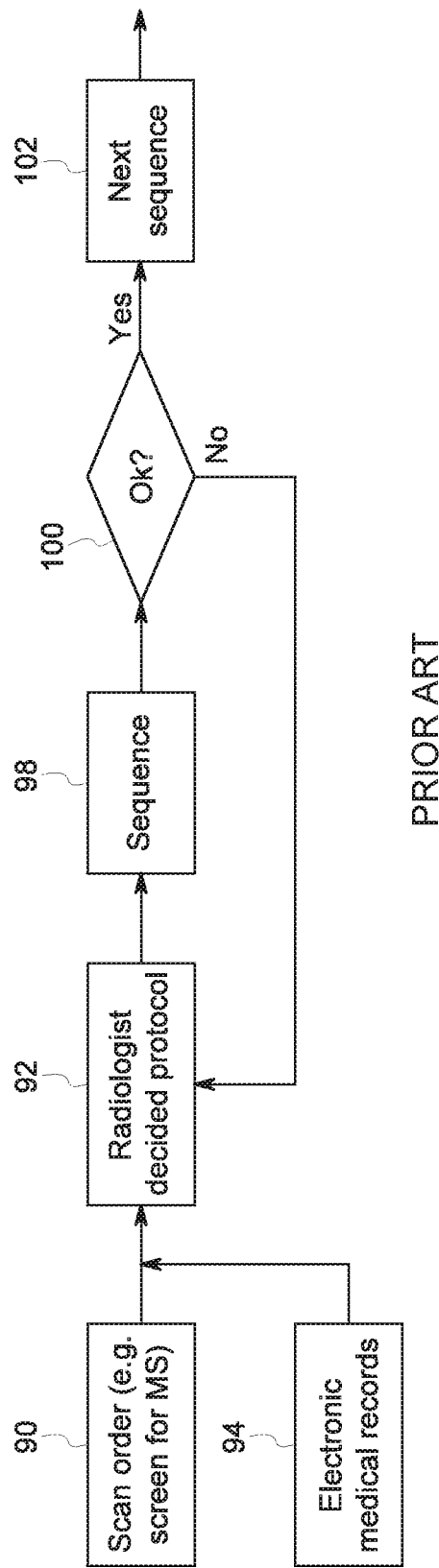
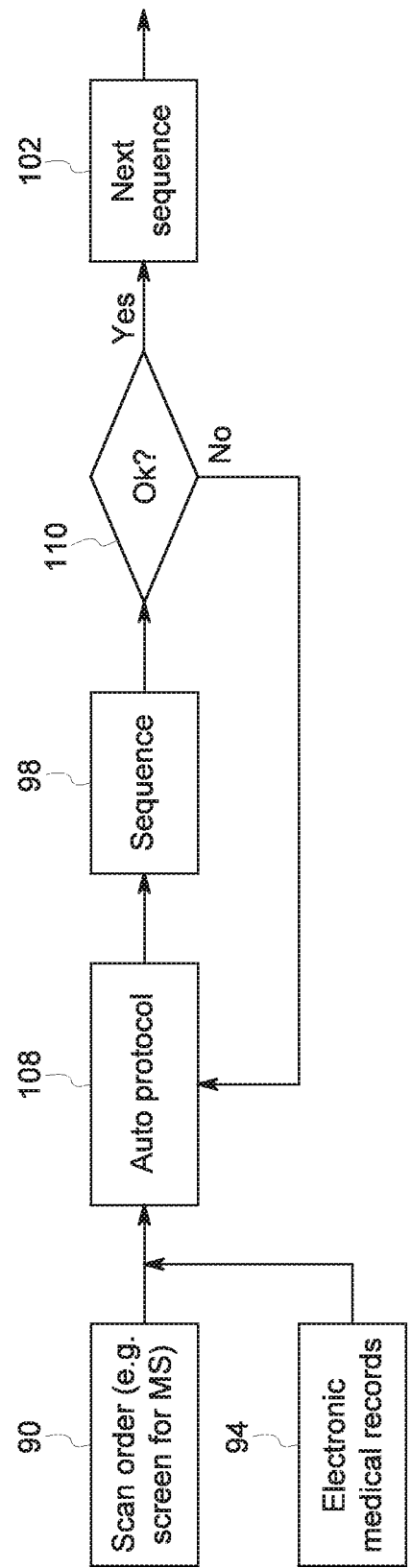
PRIOR ART
FIG. 2
FIG. 3

| | D1 | D2 | D3 | D4 | D5 | T1 with (D0-D5) | T2 with (D0-D5) | T3 with (D0-D5) | T4 with (D0-D5) | DL (t=0.5) | DL (t=0.1) | DL (t=0.8) |
|---|---|---|---|---|---|---|---|---|---|---|---|---|
| D0 | 0.38* (34) | 0.47* (36) | 0.55* (38) | 0.8* (44) | 0.51* (37) | 0.51* (7/5/37) | 0.72* (7/0/42) | 0.34 (2/14/33) | 0.55* (0/11/38) | 0.64* (6/3/40) | 0.59* (2/8/39) | 0.64* (9/0/40) |
| D1 | | 0.18 (25) | 0.41* (35) | 0.3 (31) | 0.3 (30) | 0.41* (14/1/34) | 0.27 (19/1/29) | 0.52* (4/5/40) | 0.8* (2/2/45) | 0.38 (15/1/33) | 0.49* (8/3/38) | 0.23 (21/1/27) |
| D2 | | | 0.37* (33) | 0.49* (37) | 0.41 (36) | 0.29 (4/13/32) | 0.45* (4/8/37) | 0.23 (0/23/26) | 0.25 (0/22/27) | 0.4* (3/11/35) | 0.31 (1/18/30) | 0.52* (4/6/39) |
| D3 | | | | 0.43* (35) | 0.31* (32) | 0.23 (11/8/30) | 0.28 (13/5/31) | 0.37* (2/13/34) | 0.58* (0/10/39) | 0.35* (10/6/33) | 0.38* (5/10/34) | 0.28* (14/4/31) |
| D4 | | | | | 0.4* (36) | 0.39* (7/8/34) | 0.66* (6/2/41) | 0.34 (1/16/32) | 0.46* (0/14/35) | 0.59* (5/5/39) | 0.48* (2/11/36) | 0.66* (7/1/41) |
| D5 | | | | | | 0.50* (4/8/37) | 0.70* (4/3/42) | 0.27 (1/19/29) | 0.37 (0/17/32) | 0.62* (3/6/40) | 0.46* (1/13/35) | 0.60* (6/3/40) |
| Statistics | D0-D5 | | | | | T1 with (D0-D5) | T2 with (D0-D5) | T3 with (D0-D5) | T4 with (D0-D5) | DL with (D0-D5) [t=0.5] | DL with (D0-D5) [t=0.1] | DL with (D0-D5) [t=0.8] |
| Cohen's kappa | 0.41 ± 0.13 | | | | | 0.39 ± 0.11 | 0.51 ± 0.21 | 0.35 ± 0.1 | 0.50 ± 0.1 | 0.50 ± 0.13 | 0.45 ± 0.1 | 0.48 ± 0.19 |
| Rescans | | | | | | 7.8 ± 4 | 8.8 ± 6 | 1.7 ± 1.4 | 0.3 ± 0.8 | 7 ± 4.7 | 3.2 ± 2.8 | 10.2 ± 2.6 |
| Recalls | | | | | | 7.2 ± 4 | 3.2 ± 2.9 | 15 ± 6.1 | 12.7 ± 6.8 | 5.3 ± 1.4 | 10.5 ± 2.1 | 2.5 ± 0.9 |
| Concordant ratings | 34.4 ± 3.8 | | | | | 34 ± 2.8 | 37 ± 5.8 | 32.3 ± 4.8 | 36 ± 6.2 | 36.7 ± 3.4 | 35.3 ± 3.2 | 36.3 ± 5.8 |
| Statistics | | | | | | T1-T4 with (D0-D5) | | | | DL with (D0-D5) [individual optimal threshold] | | |
| Agreement statistics | | | | | | 0.44 ± .17 | | | | 0.55 ± .11* | | |
| | | | | | | 34.8 ± 5.1 | | | | 38.7 ± 2.5* | | |

FIG. 5

| | D2 | D3 | D4 | D5 | T1 | T2 | T3 | T4 | DL [t=0.5] | DL [t=0.1] | DL [t=5e-4] | DL [t=1e-6] |
|---|---|---|---|---|---|---|---|---|---|---|---|---|
| D1 | 0.21 (38) | 0.41* (44) | 0.26 (40) | 0.41* (44) | 0.23 (10/0/39) | 0.06 (26/0/23) | 0.41* (5/0/44) | 0.21 (11/0/38) | 0.07 (25/0/24) | 0.14 (16/0/33) | 0.21 (11/0/38) | 0.47* (4/0/45) |
| D2 | | 0.51* (41) | 0.56* (41) | 0.63* (43) | 0.73* (2/3/44) | 0.43* (15/0/34) | 0.63* (0/6/43) | 0.79* (2/2/45) | 0.38 (15/1/33) | 0.49* (8/3/38) | 0.69* (3/3/43) | 0.56* (0/7/42) |
| D3 | | | 0.6* (43) | 0.67* (45) | 0.55* (6/1/42) | 0.15 (22/1/26) | 0.5* (3/3/43) | 0.51* (7/1/41) | 0.24 (20/0/29) | 0.24 (13/2/34) | 0.39* (8/2/39) | 0.38* (3/4/42) |
| D4 | | | | 0.7* (45) | 0.60* (4/3/42) | 0.28 (18/1/30) | 0.46* (2/6/41) | 0.67* (4/2/43) | 0.3 (17/1/31) | 0.38 (10/3/36) | 0.45* (6/4/39) | 0.37* (2/7/40) |
| D5 | | | | | 0.68* (5/0/44) | 0.13 (21/0/28) | 0.5* (3/3/43) | 0.63* (6/0/43) | 0.24 (20/0/29) | 0.35 (12/1/36) | 0.51* (7/1/41) | 0.56* (2/3/44) |
| Statistics | D1–D5 | | | | T1 with (D1–D5) | T2 with (D1–D5) | T3 with (D1–D5) | T4 with (D1–D5) | DL with (D1–D5) [t=0.5] | DL with (D1–D5) [t=0.1] | DL with (D1–D5) [t=5e-4] | DL with (D1–D5) [t=1e-6] |
| Cohen's kappa | 0.5 ± 0.17 | | | | 0.56 ± 0.2 | 0.21 ± 0.15* | 0.5 ± 0.08 | 0.56 ± 0.22 | 0.25 ± 0.11* | 0.32 ± 0.13 | 0.45 ± 0.17 | 0.47 ± 0.09 |
| Rescans | | | | | 5.4 ± 3 | 20.4 ± 4.2 | 2.6 ± 0.8 | 6 ± 3.4 | 19.4 ± 3.8 | 11.8 ± 1.4 | 7 ± 2.9 | 2.2 ± 1.5 |
| Recalls | | | | | 1.4 ± 0.7 | 0.4 ± 0.2 | 3.6 ± 1.1 | 1 ± 0.4 | 0.4 ± 0.2 | 1.8 ± 1.3 | 2 ± 1.6 | 4.2 ± 3 |
| Concordant ratings | 42.4 ± 2.3 | | | | 42.2 ± 2 | 28.2 ± 4.1* | 42.8 ± 1.1 | 42 ± 2.6 | 29.2 ± 3.3* | 35.4 ± 1.9* | 40 ± 2 | 42.6 ± 1.9 |
| Statistics | | | | | | | T1–T4 with (D1–D5) | | | | DL with (D0–D5) [individual optimal threshold] | |
| Agreement statistics | | | | | | | 0.46 ± 0.22 / 38.8 ± 6.8 | | | | 0.51 ± 0.12 / 42 ± 2.8 | |

FIG. 6

AUTOMATED SCANNING WORKFLOW

The subject matter disclosed herein relates to improving workflow associated with medical imaging or scanning procedures.

BACKGROUND

Non-invasive imaging technologies allow images of the internal structures or features of a patient or subject to be obtained. In particular, such non-invasive imaging technologies rely on various physical principles, such as the paramagnetic properties of tissues within the subject, the differential transmission of X-ray photons through an imaged volume, the emission of gamma rays by a radiopharmaceutical differentially distributed in the body, or the reflection of acoustic waves by structures within the body, to acquire data and to construct images or otherwise represent the internal features of the subject.

With respect to the workflow associated with an imaging scanner, certain issues may be present. For example, an on-call radiologist may spend significant time to determine an imaging protocol, which consists of a series of imaging acquisitions (to be scanned) for each individual patient. That is, it may take time to configure or prescribe the appropriate examination series for a patient. Further, a technologist may re-scan a patient one or more times to acquire better images when in fact the current acquired images are sufficient for the diagnostic purpose. Conversely, a technologist may fail to re-scan a patient when the current acquired images are not sufficient for the diagnostic purpose, which may result in the patient having to return to the facility for a second round of imaging. Lastly, when artifacts are present or likely in the images, an imaging protocol may be selected that is not tolerant to the artifact source, resulting in images containing artifacts.

BRIEF DESCRIPTION

In one embodiment, an image analysis system is provided. In accordance with this embodiment, the imaging system comprises circuitry configured to receive and process imaging data acquired by one or more scan components of the imaging system. In accordance with this embodiment, the circuity is configured to: automatically evaluate the diagnostic utility of one or more images of an imaging sequence based on a diagnostic purpose or on a combination of the diagnostic purpose and a specified reviewer. The circuitry is further configured to, upon a determination that the one or more images do not meet a threshold established for the diagnostic purpose or for the combination of the diagnostic purpose and the specified reviewer, indicate that a re-scan is needed. A re-scan is defined as the need to repeat an imaging acquisition or to perform a similar image acquisition to acquire images of sufficient image quality to render an accurate diagnosis.

In a further embodiment, a method is provided for imaging a patient. In accordance with this embodiment, one or more images of an imaging sequence are acquired using an imaging system. The one or more images are provided as inputs to an evaluation algorithm. The evaluation algorithm evaluates the diagnostic utility of one or more images based on a diagnostic purpose or on a combination of the diagnostic purpose and a specified reviewer. Upon a determination by the evaluation algorithm that the one or more images do not meet a threshold established for the diagnostic purpose or for the combination of the diagnostic purpose and the specified reviewer, a re-scan indication is provided.

In an additional embodiment, a non-transitory, computer-readable medium is provided that stores instructions executable by circuitry of an imaging system. The instructions comprise: instructions to evaluate the diagnostic utility of one or more images of an imaging sequence acquired by the imaging system based on a diagnostic purpose or on a combination of the diagnostic purpose and a specified reviewer; and instruction to provide a re-scan indication upon a determination that the one or more images do not meet a threshold established for the diagnostic purpose or for the combination of the diagnostic purpose and the specified reviewer.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2 depicts a conventional scanning workflow;

FIG. 3 depicts a scanning workflow in accordance with aspects of the present disclosure;

FIG. 5 depicts a matrix documenting Cohen's kappa scores and the number of series for which raters agree on diagnostic utility of images, assuming the series were scanned to rule out MS, in accordance with aspects of the present disclosure; and FIG. 6 depicts a matrix documenting Cohen's kappa scores and the number of series for which raters agree on diagnostic utility of images, assuming the series were scanned to rule out stroke, in accordance with aspects of the present disclosure.

DETAILED DESCRIPTION

Figure 1:
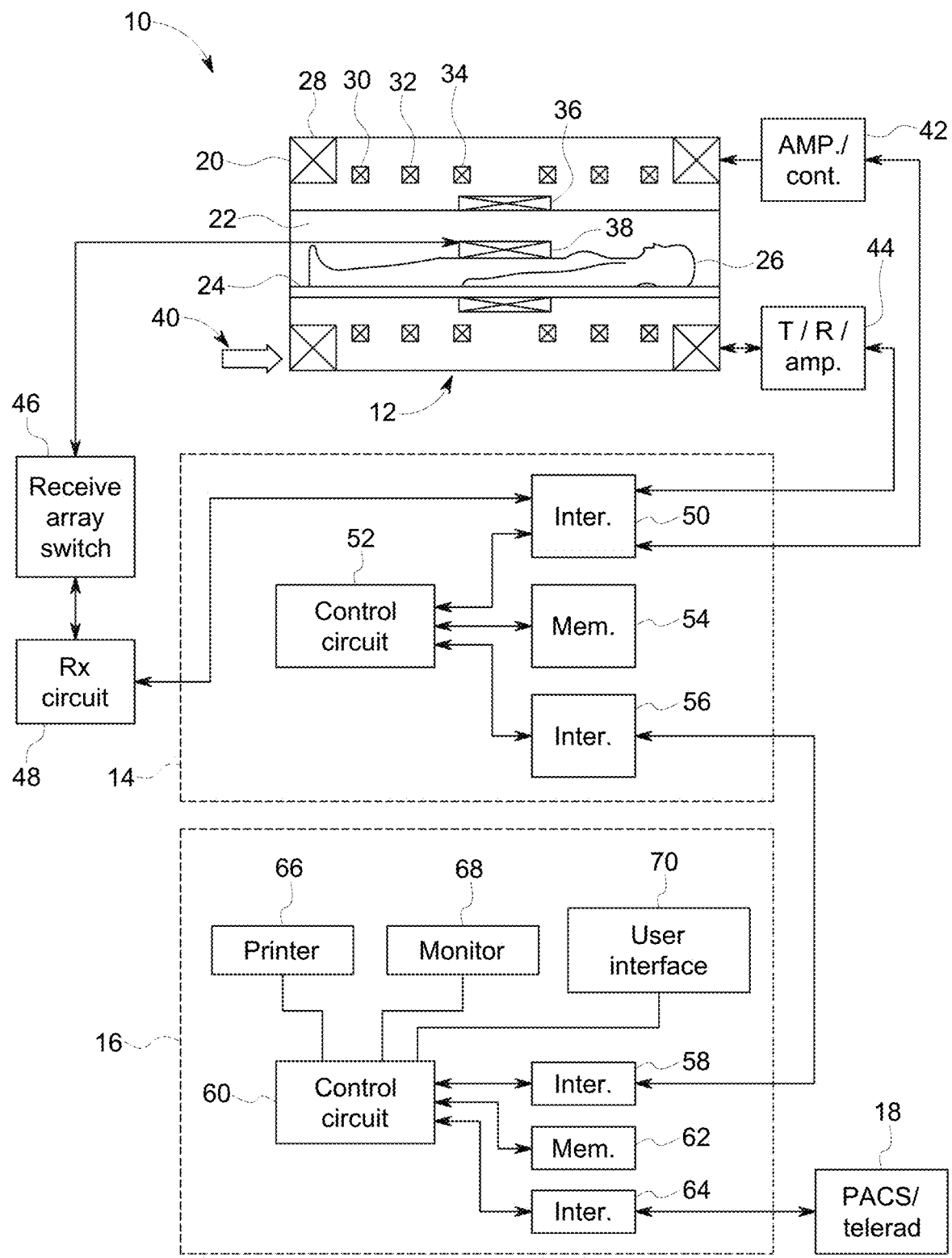
FIG. 1 illustrates an embodiment of a magnetic resonance imaging (Mill) system, in accordance with an aspect of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The high resolution and versatile contrast of magnetic resonance imaging (MRI) make it a suitable choice to diagnose neurological disorders. In the context of acquiring a diagnostic set or series of images, imaging series are typically repeated when the scanning technologist decides that diagnostic utility of an image or images of a respective series is insufficient to make the intended diagnosis due to reasons such as patient motion, metal artifacts, incorrect positioning of the field of view, hardware failures, etc. The converse problem, in which the patient is sent home with the technologist assessing that diagnostic utility of the images is sufficient for the intended diagnostic purpose, then recalled for a re-scan due to the radiologist's being unable to make a diagnosis using the acquired images, although less documented, also exists. Right-sizing or optimizing the number of re-scans is important to optimize the healthcare system's efficiency by ensuring that only the series that need to be repeated are repeated and that nobody is sent home after acquisition of images having insufficient diagnostic utility. This problem, however, is not trivial to solve, as it is the reading radiologist who ultimately decides if diagnostic utility of the images is sufficient and it is the scanning technologist who makes the re-scan decision at the time of imaging. The reading radiologist is not typically present to advise on diagnostic utility of the images at the time of image acquisition, i.e., prior to the exam's completion. In addition, radiologists may express different opinions when assessing diagnostic utility or diagnosing disease. That is, it is possible that a given image may have sufficient diagnostic utility for one doctor, but be insufficient for another. Note that in right-sizing the number of re-scans, this means that re-scans are only performed for a valid clinical purposes where there is missing information or the acquired images do not have sufficient image quality or diagnostic utility to render an accurate clinical diagnosis.

In accordance with the present disclosure, a methodology is provided for simplifying a scanner workflow associated with image acquisition. In one aspect, imaging protocols may be decided automatically based on the scanning order from the doctor or on a combination of the scanning order in conjunction with patient (electronic) medical records. In conventional workflows, determining the imaging protocol can be a time-consuming process, where the radiologist on-call decides the imaging protocols for each exam to be scanned. In addition, in one implementation, as the exam starts and each image series is scanned by the operator of the imaging system (e.g., a technologist), an automated process determines if the diagnostic utility of an acquired image is sufficient for diagnosing the suspected disease for which the patient was referred for a scan. As different radiologists have different demands for image imperfections and/or artifacts, this assessment can be made generically, considering the reasons for which the patient was scanned (i.e., the diagnostic purpose), but with no information about who will be reading the exam. By way of example, such a diagnostic purpose may correspond to a disease state or anatomical or physiological condition for which the patient is being evaluated. Alternatively, information regarding who the reading radiologist is for the respective scan can be used to reduce re-scans and recalls, while still providing the doctors with sufficient information for making a diagnosis. Should diagnostic utility of an image be sufficient for the given indication, the exam will proceed as per initial imaging protocol, e.g., the operator may be provided with an indication to proceed to the next sequence (i.e., a proceed indication). Should diagnostic utility of the image be deemed insufficient, the source of any artifacts may be identified and an indication may be provided to the technologist to repeat the imaging sequence (i.e., a re-scan indication), including in some implementation a suggestion for an alternative imaging protocol to address the artifact. By way of example, such an alternative imaging protocol may results in comparable image contrast, but be less sensitive to the source of the artifact identified in the prior scan (e.g. patient motion, metal artifacts, incorrect positioning of the field of view, hardware failures, low SNR, etc.).

With the above in mind, the present disclosure provides, in certain implementations, rule-based or deep learning-based approaches capable of assessing diagnostic utility of images (irrespective of contrast, anatomy, or orientation) in near real time. Diagnostic utility may be assessed automatically in such an approach based on one or both of the diagnostic purpose of the image(s) and/or knowledge of the reading doctor. As used herein, diagnostic purpose corresponds to a disease state or anatomical or physiological condition for which the patient is being evaluated. In particular, in one implementation, the performance of such algorithms may be validated against ratings of multiple scanning technologists and radiologists, and as a function of scan indication (i.e., diagnostic purpose for acquiring the image(s)). While large disagreements exist in diagnostic utility ratings of different radiologists in images with low or moderate artifact levels, it was determined in studies performed in support of the present disclosure that the agreement between the algorithm and each doctor can be significantly higher (as evidenced by Cohen's kappa) than the agreement between multiple radiologists in rating the same image sets. Correspondingly, an automated implementation of such an algorithm on the scanner effectively emulates the doctor himself rating images in real time, and reduce the number of unneeded re-scans and recalls. Thus, as discussed herein, diagnostic utility of an image is not an absolute measure, but instead depends upon the reading radiologist and the scan indication (i.e., the diagnostic purpose of the scan). Therefore, adapting the threshold (i.e., probability of an imaging volume being deemed good) as a function of rating doctor and scan indication can result in reducing the number of re-scans and recalls. In accordance with this approach, these two variables can be supplied to the scanner console similarly to how the prescribing doctor information is currently provided.

Though MRI examples are discussed herein, it is to be understood that the present invention may be similarly implemented using different types of image datasets, including datasets acquired using other MRI imaging protocols and/or other imaging modality types and protocols, including computed tomography (CT), tomosynthesis, mammography, ultrasound, positron emission tomography (PET), single photon emission computed tomography (SPECT), and so forth. Thus, the present disclosure is not restricted to MRI scan workflows or images, but may be implemented with respect to other image modalities as well.

The workflows described herein may be performed by an imaging system (e.g., a magnetic resonance imaging (MRI) system) in which specific imaging routines (e.g., diffusion MRI sequences) are administered by a technologist. Thus, the imaging system may perform data acquisition and data/image reconstruction under the guidance of the technologist. Accordingly, to provide context with respect to the present MRI examples, an MRI system 10 is described in FIG. 1. As may be appreciated other imaging modalities may have corresponding functional components and modules, such as detection components, command and control circuitry, data acquisition components, data processing and visualization components, and so forth. A magnetic resonance imaging system 10 is illustrated schematically by way of example of such generalized imaging systems and is depicted as including a scanner 12, scanner control circuitry 14, and system control circuitry 16. According to the embodiments described herein, the MRI system 10 is generally configured to perform MR imaging.

System 10 additionally includes remote access and storage systems or devices such as picture archiving and communication systems (PACS) 18, or other devices such as teleradiology equipment so that data acquired by the system 10 may be accessed on- or off-site. In this way, MR data may be acquired, followed by on- or off-site processing and evaluation, such as by a doctor, as discussed herein. While the MRI system 10 may include any suitable scanner or detector, in the illustrated embodiment, the system 10 includes a full body scanner 12 having a housing 20 through which a bore 22 is formed. A table 24 is moveable into the bore 22 to permit a patient 26 to be positioned therein for imaging selected anatomy within the patient.

Scanner 12 includes a series of associated coils for producing controlled magnetic fields for exciting the gyromagnetic material within the anatomy of the subject being imaged. Specifically, a primary magnet coil 28 is provided for generating a primary magnetic field, BO, which is generally aligned with the bore 22. A series of gradient coils 30, 32, and 34 permit controlled magnetic gradient fields to be generated for positional encoding of certain of the gyromagnetic nuclei within the patient 26 during examination sequences. A radio frequency (RF) coil 36 is configured to generate radio frequency pulses for exciting the certain gyromagnetic nuclei within the patient. In addition to the coils that may be local to the scanner 12, the system 10 also includes a set of receiving coils 38 (e.g., an array of coils) configured for placement proximal (e.g., against) to the patient 26. As an example, the receiving coils 38 can include cervical/thoracic/lumbar (CTL) coils, head coils, single-sided spine coils, and so forth. Generally, the receiving coils 38 are placed close to or on top of the patient 26 so as to receive the weak RF signals (weak relative to the transmitted pulses generated by the scanner coils) that are generated by certain of the gyromagnetic nuclei within the patient 26 as they return to their relaxed state.

The various coils of system 10 are controlled by external circuitry to generate the desired field and pulses, and to read emissions from the gyromagnetic material in a controlled manner. In the illustrated embodiment, a main power supply 40 provides power to the primary field coil 28. A driver circuit 42 provides power to pulse the gradient field coils 30, 32, and 34. Such a circuit may include amplification and control circuitry for supplying current to the coils as defined by digitized pulse sequences output by the scanner control circuit 14, which in one embodiment may be a diffusion imaging module. Another control circuit 44 is provided for regulating operation of the RF coil 36. Circuit 44 includes a switching device for alternating between the active and inactive modes of operation, wherein the RF coil 36 transmits and does not transmit signals, respectively. Circuit 44 also includes amplification circuitry configured to generate the RF pulses. Similarly, the receiving coils 38 are connected to switch 46, which is capable of switching the receiving coils 38 between receiving and non-receiving modes. Thus, the receiving coils 38 resonate with the RF signals produced by relaxing gyromagnetic nuclei from within the patient 26 while in the receiving mode, and they do not resonate with RF energy from the transmitting coils (i.e., coil 36) so as to prevent undesirable operation while in the non-receiving mode. Additionally, a receiving circuit 48 is configured to receive the data detected by the receiving coils 38, and may include one or more multiplexing and/or amplification circuits.

It should be noted that while the scanner 12 and the control/amplification circuitry described above are illustrated as being coupled by a single line, that many such lines may occur in an actual instantiation. For example, separate lines may be used for control, data communication, and so on. Further, suitable hardware may be disposed along each type of line for the proper handling of the data. Indeed, various filters, digitizers, and processors may be disposed between the scanner and either or both of the scanner and system control circuitry 14, 16. By way of non-limiting example, certain of the control and analysis circuitry described in detail below, although illustrated as a single unit, includes additional hardware such as image reconstruction hardware configured to perform data processing.

As illustrated, scanner control circuit 14 includes an interface circuit 50, which outputs signals for driving the gradient field coils and the RF coil and for receiving the data representative of the magnetic resonance signals produced in examination sequences. The interface circuit 50 is coupled to a control and analysis circuit 52. The control and analysis circuit 52 executes the commands for driving the circuit 42 and circuit 44 based on defined imaging protocols selected via system control circuit 16. Control and analysis circuit 52 also serves to receive the magnetic resonance signals and performs subsequent processing before transmitting the data to system control circuit 16. Scanner control circuit 14 also includes one or more memory circuits 54, which store configuration parameters, pulse sequence descriptions, examination results, and so forth, during operation. By way of example, code or routines may be stored in the memory circuits 54 and executed by the control circuit 14 as part of implementing aspects of the present disclosure.

Interface circuit 56 is coupled to the control and analysis circuit 52 for exchanging data between scanner control circuit 14 and system control circuit 16. In certain embodiments, the control and analysis circuit 52, while illustrated as a single unit, may include one or more hardware devices. The system control circuit 16 includes an interface circuit 58, which receives data from the scanner control circuit 14 and transmits data and commands back to the scanner control circuit 14. The interface circuit 58 is coupled to a control and analysis circuit 60 which may include a CPU or other microprocessor architecture that may be present in a multi-purpose or application specific computer or workstation. Control and analysis circuit 60 is coupled to a memory circuit 62 to store programming code for operation of the Mill system 10 and to store the processed image data for later reconstruction, display and transmission. The programming code may execute one or more algorithms that, when executed by a processor, are configured to perform reconstruction of acquired data and may further include algorithms for generating images. By way of example, code or routines may be stored in the memory circuits 62 and executed by the control and analysis circuit 60 as part of implementing aspects of the present disclosure.

An additional interface circuit 64 may be provided for exchanging image data, configuration parameters, and so forth with external system components such as remote access and storage devices 18. Finally, the system control and analysis circuit 60 may include various peripheral devices for facilitating operator interface and for producing hard copies of the reconstructed images. In the illustrated embodiment, these peripherals include a printer 66, a monitor 68, and user interface 70 including devices such as a keyboard or a mouse.

It should be noted that the MRI system described is provided merely as an example. Other types of MRI systems (e.g., "open" MRI systems) as well as other imaging modalities may be employed with the present invention.

With the preceding in mind, the following issues may arise in the context of a scanner workflow for imaging a patient using an imaging system such as the MRI system described above.

(1) The radiologist on-call spends significant time to define the imaging protocol (which consists of a series of imaging acquisitions) to be scanned for each individual patient. By taking the scan order from the referring doctor as input, and examining/referring to the patient's medical records, the radiologist decides which series or type(s) of acquisition should be scanned in each exam and for each patient.

(2) The imaging series are re-scanned when diagnostic utility is sufficient for diagnostic purposes (e.g., false negative assessment for adequate image quality). If a certain artifact is present in the images, the technologist performing the scan has to decide whether diagnostic utility is adequate for clinical diagnosis, depending on the diagnostic purpose of the exam, or if the scan or imaging series should be repeated. In many cases, the technologist choses to repeat a series whose diagnostic utility was in fact adequate for the diagnostic purpose, unnecessarily lengthening the imaging exam and incurring unnecessary expenses for the health care system.

(3) Scans are not re-scanned when diagnostic utility is insufficient for diagnostic purposes (e.g., false positive assessment for adequate image quality). As above, should an artifact be present in an image, the technologist may decide that diagnostic utility is sufficient for the diagnostic purpose, and decide to proceed with an exam without repeating a given imaging series. Should the reading radiologist later decide that diagnostic utility was, in fact, insufficient, the patient would have to be recalled for a second imaging scan, delaying the diagnosis, creating significant inconvenience to the patient and increasing the total cost of the exam (it takes significantly less time to repeat a series at the time its quality is deemed insufficient than to schedule an entire new exam for that patient).

(4) An imaging protocol tolerant to a present artifact source is not chosen. While in some cases the technologist adequately decides that a series should be repeated, he or she may repeat the scan with the same initial type of imaging sequence or an alternative one that is not tolerant to the source of an artifact present in the image, such as a motion artifact or metal artifact.

With the preceding in mind, the present disclosure relates to a simplified scanner workflow suitable for use with MRI or other imaging modality acquisitions. In conventional workflows, determination of imaging protocols can be a time-consuming process, where the radiologist on-call decides the protocols for each exam to be scanned. In one aspect of the present disclosure, imaging protocols are instead decided automatically based on: (1) a scanning order or prescription or (2) a scanning order in conjunction with patient (electronic) medical records.

In a further aspect, as the exam starts and each series is scanned by the technologist, an automated process determines if diagnostic utility of the images is sufficient for diagnosing the suspected disease for which the patient was referred for a scan. As different radiologists have different tolerances for image imperfections and/or artifacts, this assessment can be made generically, considering the reasons for which the patient was scanned (i.e., the scan order), but with no information about who will be reading the exam. Alternatively, information regarding who the reading radiologist is for the respective scan can be used to decrease re-scans and recalls, while still providing the doctors with sufficient information for making a diagnosis. Should diagnostic utility be sufficient in an imaging series for the given indication, the exam will proceed as per initial imaging protocol.

In an additional aspect, should diagnostic utility be deemed insufficient, the source of the artifact will be identified, and the technologist can be provided with a suggestion for an alternative imaging protocol to address the artifact. By way of example, the alternative imaging protocol may provide comparable image contrast but be less sensitive to the source of the artifact identified in the prior scan (e.g. motion, metal artifact, low SNR, etc). In certain aspects, the imaging protocol may be automatically adapted or parameterized, such as using rule-based or deep-learning approaches, to address the artifact.

Thus, aspects of the present disclosure may be understood to employ some number of automated algorithms that perform one or more of: (1) simplifying and/or automating the imaging protocol determination, thereby reducing or eliminating the time that the reading radiologist spends to decide what series to be scanned; (2) automatically determining whether diagnostic utility of an acquired image is sufficient for the given scan indication (e.g., diagnostic purpose) and/or reading radiologist; and/or (3) automatically suggesting an alternative imaging protocol or re-parameterizing an existing imaging protocol that is less sensitive to the source of an artifact.

With this in mind, FIG. 2 depicts a conventional imaging scanner workflow. In accordance with this workflow a scan order 90 (e.g., an instruction or prescription to screen for multiple sclerosis in the depicted example) from a referring doctor is provided to a radiologist (e.g., an on-call radiologist) to determine (block 92) an imaging protocol (e.g., scan sequence 98) defining a series of images to be acquired of the patient. The radiologist may also rely on medical records (e.g., electronic medical records 94) having data on patient medical history and/or characteristics in deciding the imaging protocol. In the depicted conventional approach, the technologist makes a subjective determination 100 whether the image(s) obtained in accordance with the imaging protocol are of sufficient quality or not. In a conventional approach, the determination 100 made by the technologist may be largely or entirely independent of the diagnostic purpose underlying the scan order 90 (i.e., the diagnosis to be made based on the acquired images) and/or of the radiologist who will read the acquired images. As a result, unnecessary re-scans and patient recalls may occur. If the technologist determines that the acquired images are of insufficient quality, the imaging sequence 98 is repeated (i.e., a re-scan) using the same imaging protocol or a replacement protocol (such as to address an artifact in the images), at the technologist's discretion. If the technologist determines that the acquired images are of sufficient quality, the technologist proceeds to the next image sequence 102 or concludes the scan operation.

Conversely, FIG. 3 depicts an imaging scanner workflow employing some or all of the algorithms noted above. As in the conventional approach, the process may be initiated based on a scan order 90 or a combination of scan order 90 and electronic medical records 94. As opposed to an on-call radiologist generating the imaging protocols from these materials, a rule-based or trained deep-learning algorithm may receive these materials as inputs and generate the imaging protocol (e.g., sequence 98) automatically (denoted as "auto protocol" 108 in FIG. 3). As in the conventional approach, a technologist may acquire images based on the imaging protocol (i.e., sequence 98). Unlike the conventional approach, in certain implementation of the present invention, a determination 110 is made automatically (using rule-based or deep-learning approaches) as to whether the obtained in accordance with the imaging protocol are of sufficient quality or not. In such an embodiment, and unlike conventional approaches, the determination 110 may be based on one or both of the scan indication (i.e., diagnostic purpose of the scan) and/or the radiologist who will be reviewing the images. As a result, unnecessary re-scans and patient recalls may be reduced. If the automated algorithm determines that the acquired images are of insufficient quality, another automated algorithm, in one embodiment, may determine reason(s) for insufficient image quality for the diagnostic purpose and may either determine or suggest a change to the imaging protocol for re-scanning. In this manner, the likelihood of obtaining suitable image is increased, such as by using a scan imaging protocol capable of addressing the source of an image artifact. Conversely, if the automated decision process determines that the acquired images are of sufficient quality, the technologist proceeds to the next image sequence 102 or concludes the scan operation.

With the preceding in mind and the flow depicted in FIG. 3, technical benefits of the present disclosure may be understood to include some of all of: (1) decreasing the time a radiologist may spend to determine the imaging protocol an imaging exam for a given patient or removing this task altogether from the to-do list of the radiologist on-call; (2) reducing the number of re-scans and recalls (i.e., an image series will only be re-scanned if the diagnostic utility of the image(s) is deemed insufficient by an unbiased assessment (e.g., automated and/or algorithmic assessment) that takes into account the diagnostic purpose of the scan solely or in combination with information about the reading radiologist, and/or (3) choosing a new imaging protocol or modifying the current imaging protocol for a re-scan to mitigate artifact(s) identified in the initial image series. These three aspects are discussed in greater detail below.

With respect to automated determination of the imaging protocol, in one example doctor scan orders or doctor scan orders in conjunction with patient medical records are converted into or otherwise used to automatically generate a scanning (imaging) protocol. This can be done in an automated manner using a set of deterministic rules or by a machine learning algorithm.

With respect to imaging protocol adaptation or re-parameterization for re-scans, once diagnostic utility of an image is deemed insufficient by upstream algorithm(s), a further algorithm (e.g., a rule-based or machine learning based algorithm) may suggest an alternative series to be scanned that is less sensitive to the source of artifact identified above.

With respect to deciding if diagnostic utility of an image or image series is sufficient to diagnose a certain condition, generically or by a given radiologist, one or more algorithms may be employed as part of this determination. As discussed herein, the answer to whether a given image or image series has sufficient diagnostic utility will depend on the indication for which the patient is scanned for (i.e., the diagnostic purpose) and, in some instance, who the reading radiologist is. With this in mind, in the present disclosure, two separate approaches are contemplated to rate diagnostic utility. In certain embodiments described herein, two-dimensional images are provided as inputs and a probability of an image to be good (i.e., P(good)) (i.e., have diagnostic utility to a generic or specific reading doctor) is provided as an output. Once ratings are generated for all images in an imaging volume, a rating per volume can correspondingly be generated based on the collective ratings. This can be obtained, in one implementation, through an arithmetic mean or a geometric mean of the probabilities for each individual slices. The rating per volume is then compared to a threshold, which can be a function of scan indication or scan indication and reading radiologist. For example, volumes in which ratings for different slices vary significantly are usually rated badly. With enough training data for the underlying algorithm, an approach in which volumetric datasets (or fractions of volumetric datasets) are used as input instead of single, two-dimensional slices may be implemented.

With respect to the two contemplated approaches, in a first algorithm-based approach deterministic features are extracted from individual images or from the headers of the files. This can include, but is not limited to, image features characterizing signal, noise, image focus, edges, texture, etc. In an MRI context, features from the headers of the file, including the type of contrast (T1/T2), echo time (TE), repetition time (TR), field strength, etc. can also be included. A support vector machine (SVM) performs the classification, outputting the probability for an image to be good (P(good)). In embodiments discussed herein, this algorithm will be referred to as SVM.

In a second algorithm approach, a convolution neural network (CNN) is used for feature extraction, using the same single slice images, followed by a fully connected neural network for classification. In embodiments discussed below, this algorithm will be referred as deep learning (DL).

With the preceding in mind, a study was performed to evaluate a deep learning approach as presently contemplated. This study used retrospective data in the form of consecutive brain data from patients scanned on three 1.5T scanners to train a deep learning algorithm, as described herein. Data was purposely enriched in exams that contained at least one repeated series by ceasing accumulation of no-repeat exams, then only including ensuing series that were repeated. Imaging series repeated due to any reason were initially accepted in the study. It was found that the main reason to re-scan a brain series was patient motion (~95%). The remainder of repeated series were due to low signal to noise ratio (SNR) or metal artifacts. Due to this natural data segregation, only motion corrupted data sets were included in the CNN training and testing. Anatomical images of all orientations (sagittal, axial and coronal), all contrast types (proton density, T1, T2, T2* and FLAIR) and all pathologies were included. Diffusion weighted images were excluded. Detecting motion in such images is considerably simpler, due to the inherent phase striping pattern emerging in moving patients.

Data was initially rated by a single reader who rated images into three categories: 1 (clinically good (CG)), 2 (questionable), and 3 (clinically bad (CB)). The "questionable" data (initial class 2 rating) was sent to an additional radiologist who re-rated images into CG (no repeat) and CB (repeat) categories. The second radiologist was also provided with a scan indication (e.g., multiple sclerosis (MS)). Images covered all scan planes, ages, and pathologies. Overall, 9554 images belonging to the clinically good group and 7783 images belonging to the clinically bad group were used for training a deep learning algorithm. The purpose for this 2-tiered rating was that a data set enriched in questionable datasets (i.e. category 2) was intended to be set aside for testing and further MRI technologist/radiologist rating since making the right re-scan decisions for these types of data sets was of particular interest.

Figure 4:
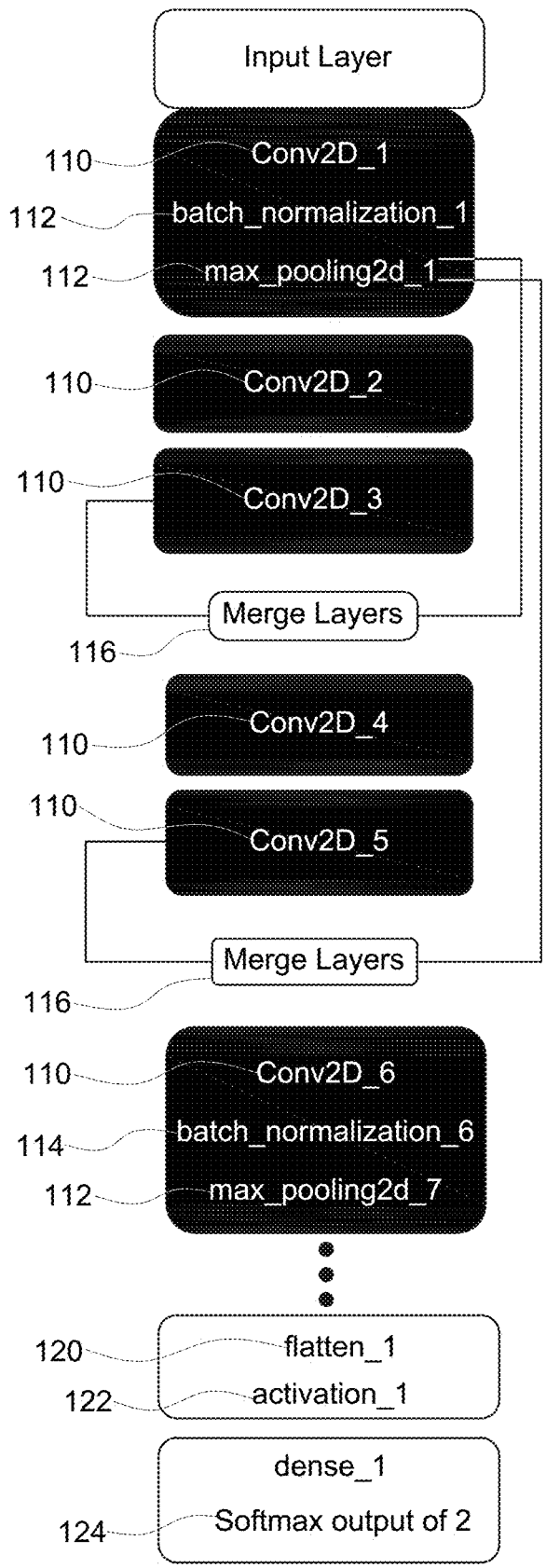
FIG. 4 depicts a convolutional neural network architecture, in accordance with aspects of the present disclosure.

With respect to the deep learning base classification tested in the study, the overall deep learning based workflow is depicted in FIG. 4. In this example, a 2D-classification model with a Tensorflow backend was trained to classify MRI slices into good (i.e., classification good (CG)) or bad (i.e., classification bad (CB)). The architecture of the convolution neural network (CNN) is illustrated in FIG. 4. In the described example, the deep learning architecture has seven convolutional layers 110, four max pooling layers 112, and three batch normalization layers 114, though other layer configurations and numbers may alternatively be employed. The dots between the layers labeled max_pooling_7 and flatten_1 represent another block containing the $7^{th}$ 2 D convolution layer, the $7^{th}$ batch normalization layer and the $8^{th}$ max_pooling layer.

The activation function, a non-linear exponential linear unit, helps learn complex patterns from data. In this example, to enhance dominant features, two merge layers 116 were introduced using the multiplication operation. At the end of all the convolutional layers, a "flatten" layer 120 was employed, which converts the feature tensor from convolutional layers to a 1-D tensor. A "tan h" activation 122 was followed by a fully connected layer and "softmax" output 124. The fully connected layer further helps learn the non-linear combinations of features provided by CNN layers. Softmax function provides probabilities for each class, with the sum of the probabilities equaling 1. In this example, categorical cross-entropy was used as loss function and optimizer was set to "rmsprop". For the purpose of the study discussed herein, images used for training and testing were converted to a size of 128×128 and pixel values were transformed into z-score maps (defined as ($pixel_{value}$−mean (series))/standard_deviation(series).

The deep learning model as shown in the present example outputs a probability for each slice belonging to the CG class. In practice, re-scan decisions are typically made on a per-series, not per-slice basis. Therefore, in this example individual slice ratings were pooled to compute a per-series score, expressed as the geometric mean of the per-slice probabilities (P(series)=$\sqrt{P1 \cdot P2 \cdot ... \cdot Pn}$, where P1, P2, ... Pn are predictions for slices 1, 2, ... n). Finally, a series is rated as CG if P(series) is greater or equal than a given threshold t, and as CB is P(series) is smaller than the same threshold t.

Out of the initial data sets, 49 series not included in training (1344 images of all orientations, contrast types and pathologies) were set aside for deep learning classification testing. This series was also sent to five radiologists and four MRI technologists. This data set predominantly consisted of images with low or moderate levels of artifact: Out of the 49 series, 5 were initially rated as bad, 6 were initially rated as good, and 38 series were initially rated as questionable. All nine survey participants were asked to rate images as CG (no need to re-scan) or CB (re-scan needed), assuming that the patients were scanned to: a) rule out stroke and b) to rule out multiple sclerosis (MS). Stroke is an indication usually requiring lower image quality, while MS is an indication requiring higher image quality.

It was observed that doctors will change their diagnostic utility rating of an image or images, depending on the purpose of the scan, significantly more often than technologists (doctors: 36%, technologists: 11%). Table 1, below, depicts the % of ratings that differ based on indication (stroke versus MS), with D1-D5 representing the doctors and T1-T4 representing the technologists. As a consequence, scan orders or keywords from orders (i.e., the diagnostic purpose of the scan) may be useful as input to an algorithm in order to generate meaningful ratings. That is, the concept of sufficient or insufficient diagnostic utility may not be meaningful in the absence of a scan indication or diagnostic purpose.

TABLE 1

|  | D1 | D2 | D3 | D4 | D5 | T1 | T2 | T3 | T4 |
|---|---|---|---|---|---|---|---|---|---|
| % ratings that differ based on indication (stroke vs MS) | 22.4 | 44.9 | 32.7 | 34.7 | 46.9 | 28.6 | 6.1 | 10.2 | 0 |

A second finding was that there was relatively limited agreement between doctors and between doctors and technologists regarding whether a given series has sufficient or insufficient diagnostic utility. The summary of how many insufficient quality series were found among the 49 data sets sent out is presented in Table 2, below. which presents the results of the technologist/radiologist survey. In this table, the number of series deemed of insufficient image quality (i.e., needing re-scan) for a diagnosis as a function of scan indication, reading radiologist (D1-D5), and scanning technologist (T1-T4) is shown.

TABLE 2

|  | D1 | D2 | D3 | D4 | D5 | T1 | T2 | T3 | T4 |
|---|---|---|---|---|---|---|---|---|---|
| # of Series (out of 49) rated as re-scan, assuming patients screened for stroke | 2 | 13 | 8 | 11 | 7 | 12 | 28 | 7 | 13 |
| # of Series (out of 49) rated as re-scan, assuming patients screened for MS | 13 | 35 | 24 | 28 | 30 | 26 | 31 | 12 | 13 |
| Total # of Series requiring re-scan (out of 98) | 15 | 38 | 32 | 39 | 37 | 38 | 59 | 19 | 26 |

It may be noted that there would have been a significant number of re-scans and recalls, should no automated algorithm decide whether diagnostic utility is sufficient. For example, if the technologist T2 were scanning patients for a stroke indication, whose scans would be read by doctor D1, he or she would have re-scanned 26 (=28−2) unneeded series. Alternatively, if the technologist T3 were scanning patients for a multiple sclerosis (MS) indication, whose scans would be read by doctor D2, he or she would have sent home 23 patients (=35−12) whose series needed a repeat, causing therefore 23 unneeded recalls.

With respect to Table 2, certain observations may be made or repeated. First, doctors differ in their tolerance to artifacts. D1 (and to some extent D3) required generally lower subjective image quality of an image to perform a diagnosis than D2, D4 and D5. The artifact tolerant/intolerant doctors were not statistically different from the others in terms of years of experience. Second, radiologists have a refined view of diagnostic utility of an image depending on scan indication, i.e., the diagnostic purpose of the scan. They change their diagnostic utility rating depending on scan indication (stroke or MS) in 36% of the cases surveyed. Conversely, MRI technologists only change their assessments in 11% of the cases. Third, depending on who scans the exam, and who reads it, there can be large number of unneeded re-scans or recalls. For example, assuming that patients were screened to rule out stroke, and T2 was scanning for the reading radiologist D1, 26 (=28−2) unneeded re-scans (out of 49 scanned series) would be performed. Conversely, should the 49 patients be screened to rule out MS, and should technologist T3 be scanning for reading radiologist D2, 23 (=35−12) patients (out of 49) would be sent home with images of insufficient quality.

Given the rating variability evidenced by the survey as shown in Table 2, it appears that doctors differ in their tolerance levels for image artifacts. Consequently, following deep learning classification (which results in a probability for each slice's diagnostic utility (DU) to be sufficient), the volume probability (computed as the geometric mean of the slice probabilities) was checked against 3 different thresholds (P(good)=0.1, 0.5 and 0.8) to decide the DU rating of a given volume. The results of this comparison are shown in FIG. 5.

The table of FIG. 5 summarizes the concordance between radiologists, between radiologists and MRI technologists, and between the trained deep learning algorithm and radiologists, by displaying Cohen's kappa, assuming that patients were screened to rule out MS. For between doctor agreements, the numbers in parenthesis are the total number of series that raters agree on (out of 49). For the agreements between doctors and technologists or doctors and DL, the numbers in parenthesis represent (re-scans/recalls/number of agreements). Here re-scans represent series called good by the doctor and bad by the other rather (technologist or DL). Recall represents series called bad by the doctor and good by the other rater. The sum of re-scans, recalls and number of agreements always equals 49. Here D1-D5 and T1-T4 represent the same individuals as in Table 2, D0 is the initial doctor, whose ratings were used for deep learning algorithm training. The starred values in the first six rows represent instances where the agreement between readers was not by chance; the starred values of the bottom row indicate that the higher kappa and number of series agreed on is statistically higher (p<0.05) than those corresponding to the agreement between different radiologists.

With respect to this table, certain observations may be made or repeated. First, there are wide disagreements between doctors in this sample enriched in data sets with some level of artifact. On the average, radiologists only agree on 34/49 ratings, with an average Cohen's kappa of only 0.41. At the minimum, D1 and D2 only agreed on 25/49 ratings. At the maximum, two doctors agreed on 44/49 exams (D0 and D4). Second, the agreement between radiologists and between radiologists and MRI technologists in rating diagnostic utility is statistically equivalent. Third, for the doctor whose ratings were used to train the deep learning algorithm (D0), a threshold of 0.5 results in the best classification performance, as expected. Should one choose a single threshold for all rating doctors, the same P(good)=0.5 works best overall.

Fourth, individualized thresholds result in the best agreements between the deep learning classification algorithm and each radiologist (shaded cells in the table of FIG. 5). For example, for the more lenient doctors (D1 and D3, MS line of the table of Table 2), a low threshold of P(good)=0.1 to define images as of sufficient quality works best; for the others, higher thresholds of 0.5-0.8 will result in the highest agreement between the deep learning algorithm and their ratings. With individualized thresholds, the agreement between radiologists and deep learning rating is statistically better than the agreement between radiologists (bottom row). The use of such an automated rating procedure emulates the reader himself deciding on a re-scan, hence taking the technologist out of the equation. Such individualized thresholds may be implemented in practice. For example, once such automated rating algorithms are deployed in a hospital, each radiologist at the hospital may be asked to rate a single batch of data sets. The concordance between the deep learning algorithm and the individual doctor will be ascertained for a range of thresholds. The threshold resulting in the best deep learning-individual radiologist concordance, defining the tolerance to artifact of a given doctor for a given scan indication, could then be saved as a reference for all future exams to be reviewed by that specific doctor.

Turning to the table shown in FIG. 6, the same deep learning network, without further training, was used to classify the same 49 series. In this case, however, it was assumed that patients were scanned to rule out stroke. While in the current implementation probabilities output by the deep learning algorithm were independent of scan indication, it was thought that adapting the threshold for an imaging volume to be rated as good could compensate for the generally lower image diagnostic utility needed of a scan performed to rule out stroke. As some readers already reached their optimal thresholds at P(good)=0.1 for the MS scan indication, lower thresholds (of P(good)={0.5, 0.1, 5e-4 and 1e-6}) were explored. The table of FIG. 6 summarizes the results of this investigation. Doctor D0, whose initial ratings were used to train the deep learning algorithm is now absent as no "stroke" ratings were obtained for this reader. The starred values in the first five rows represent instances where the agreement between readers was not by chance.

With respect to this table, certain observations may be made or repeated. First, there is a generally higher agreement between doctors in calling an imaging volume good or bad for ruling out stroke (kappa increases from 0.41 for the MS scan indication to 0.5 for stroke). Second, while the agreement between MRI technologists and radiologists is still statistically equivalent (on the average) to the agreement between radiologists, one technologist was observed (T2) who would cause significantly more re-scans than needed. Third, should the same threshold of t=0.5 be used to separate sufficient from insufficient diagnostic utility images for the stroke indication, poor agreement would be obtained between the deep learning and doctors' diagnostic utility rating (Cohen's kappa=0.25). A single optimal threshold of P(good)=1e-6, consistent with the lower diagnostic utility needed of images reviewed to rule out stroke, would better separate volumes (Cohen's kappa=0.47). Fourth, as before, individualized, per doctor thresholds would result in best volume stratification, according to the individual doctor's needs. The more lenient doctors for the stroke indication (D1 and D5 of the Table 2, stroke row) need the lowest threshold setting in the deep learning output to maximize agreement, while higher thresholds (P(good)=5e-4) would result in better agreement for the stricter doctors (D2, D3, D4). Fifth, with individualized thresholds, the agreement between the dep learning algorithm and doctors and MRI technologists, although higher, does not surpass statistical significance. The use of such automated algorithm for diagnostic utility determination, however, would preclude a technologist such as T2 from scanning fifteen series more than any of the reading doctors would have asked for.

The above findings, in an MS context, are further summarized in Table 3, below. In particular, the Cohen kappa scores (determining the agreement between different raters), as well as the average number of series that readers agreed on is listed in Table 3.

TABLE 3

|  | Cohen's Kappa | # of Concordant Ratings (out of 49) |
| --- | --- | --- |
| Within (D1, D2, D3, D4, D5) | 0.36 ± .09 | 33 ± 3.7 |
| Between T1-T4 and D1-D5 | 0.42 ± .17 | 34.3 ± 3.7 |
| Between DL and D1-D5 (common optimal threshold) | 0.46 ± .2 | 35.6 ± 6.2 |
| Between DL and D1-D5 (individualized threshold) | 0.53 ± .11 (p = 0.006) | 38.4 ± 2.7 (p = 0.01) |
| Between SVM and D1-D5 (common optimal threshold) | 0.37 ± .1 | 33.4 ± 2.6 |
| Between SVM and D1-D5 (individualized threshold) | 0.41 ± .12 | 35 ± 4.2 |

Note that statistically higher concordance is obtained while using the automated DL algorithm ($3^{rd}$ row from the bottom), while adapting the threshold to each doctor's needs (i.e., individualized thresholds) than if the images were simply given to a different reading radiologist. Individualized thresholds in this example are equivalent to assigning individualized P(good) thresholds for each doctor. For example, the less demanding doctors D1 and D3 in Table 2 were assigned a threshold of P(good)=0.1, while the more demanding doctor D3 was assigned a threshold P(good) =0.8. A radiologist-specific threshold will need to be calibrated a single time once this algorithm is deployed in a specific hospital: each doctor would be given a number of series, similar to the 49-series data set used here for validation. Depending on how the doctor rated these series, a threshold will be assigned to him or her that will ensure that the optimal number of series is repeated for that particular doctor.

Note that a single-doctor, single indication rating may not be sufficient for the training of machine learning algorithms intended to rate images for different scan indications. Adapting thresholds to the level of artifact tolerance of different radiologists can generate outputs tailored to each doctor. A single condition training, however, may not be sufficient for multiple condition rating.

With this in mind, the initial algorithms may be trained for multiple scan indications. This can be done by either having specific networks trained for one scan indication, or having one single network trained for multiple indications, by inputting those ratings as specific channels. For practical implementations, all clinical indications for scans can be separated in 3-4 diagnostic utility ratings. For example: (1) the indications for which the lowest diagnostic utility would be needed might be stroke and hemorrhage; (2) the middle indication may include MS; and (3) the indications requiring the highest indications might include screening for epilepsy or brain metastases. In such an approach, all incoming scan indications would be bucketized into these specific categories, then sent to networks trained specifically for the given category.

With the preceding in mind, the determination of whether diagnostic utility of one or more images is sufficient is a function of reading doctor and scan indication (e.g., diagnostic purpose). Each reading doctor can be given a batch of series to review prior to implementing this algorithm in a hospital. Depending on how he or she rated them, the algorithm can determine a threshold that will separate sufficient from insufficient diagnostic utility images for each doctor and each scan indication. It will then keep this same threshold for all ensuing scans that will be rated by the same doctor for the same scan indication. Alternatively, continuous learning can be implemented: for each scan to be reviewed, the algorithm will perform the rating, and the doctor would have the option to agree or disagree with this rating. The additional incoming flow of data sets whose diagnostic utility was assessed by the doctor will then be used for further training and refining of the classification algorithm, to improve classification performance.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An image analysis system, comprising:
circuitry configured to receive and process imaging data acquired by one or more scan components of the imaging system, wherein the circuitry is configured to:
automatically evaluate a diagnostic utility of one or more images of an imaging sequence based on a combination of a diagnostic purpose and a specified reviewer; and
upon a determination that the one or more images do not meet a threshold established for the combination of the diagnostic purpose and the specified reviewer, provide a re-scan indication;
wherein the circuitry is further configured to automatically evaluate the diagnostic utility of one or more images by:
determining a probability of each of a plurality of images being good in an imaging volume;
determining an arithmetic mean or a geometric mean of the probabilities for the plurality of images; and
comparing the arithmetic mean or the geometric mean with the threshold.

2. The image analysis system of claim 1, wherein the image analysis system is implemented in a magnetic resonance imaging system.

3. The image analysis system of claim 1, wherein the one or more images are automatically evaluated using a rule-based algorithm or a trained deep-learning network.

4. The image analysis system of claim 1, wherein the diagnostic purpose corresponds to a disease state or an anatomical or physiological condition for which the patient is being evaluated.

5. The image analysis system of claim 1, wherein the specified reviewer comprises a reading radiologist separate from an operator acquiring the one or more images.

6. The image analysis system of claim 1, wherein the circuitry is further configured to:
receive an input comprising a scan order or the scan order and at least a portion of an electronic medical record;
in response to the input, automatically determine an imaging protocol comprising at least the imaging sequence.

7. The image analysis system of claim 1, wherein the circuitry is further configured to:
upon the determination that the one or more images do not meet the threshold established for the combination of the diagnostic purpose and the specified reviewer, further automatically provide an alternative imaging protocol for performing the image acquisition during a re-scan.

8. The image analysis system of claim 1, wherein the circuitry is further configured to:
upon a determination that the one or more images meet the threshold, providing a proceed indication to proceed to a next imaging sequence.

9. A method for imaging a patient, comprising:
acquiring one or more images of an imaging sequence using an imaging system;
providing the one or more plurality of images as inputs to an evaluation algorithm, wherein the evaluation algorithm evaluates a diagnostic utility of one or more images based on a combination of a diagnostic purpose and a specified reviewer; and
upon a determination by the evaluation algorithm that the one or more images do not meet a threshold established for the combination of the diagnostic purpose and the specified reviewer, providing a re-scan indication;
wherein the evaluation algorithm evaluates the diagnostic utility of one or more images by:
determining a probability of each of a plurality of images being good in an imaging volume;
determining an arithmetic mean or a geometric mean of the probabilities for the plurality of images; and
comparing the arithmetic mean or the geometric mean with the threshold.

10. The method of claim 9, wherein the evaluation algorithm comprises one of a rule-based algorithm or a deep-learning network.

11. The method of claim 9, wherein the diagnostic purpose corresponds to a disease state or an anatomical or physiological condition for which the patient is being evaluated.

12. The method of claim 9, wherein the specified reviewer comprises a reviewing physician separate from an operator acquiring the plurality of images.

13. The method of claim 9, further comprising:
receiving a scan order or the scan order and at least a portion of an electronic medical record;
in response to the scan order or the scan order and at least the portion of the electronic medical record, automatically determining an imaging protocol comprising at least the imaging sequence.

14. The method of claim 9, further comprising:
upon the determination that the one or more images do not meet the threshold established for the combination of the diagnostic purpose and the specified reviewer, further providing an alternative imaging protocol for performing the image acquisition during a re-scan.

15. The method of claim 9, further comprising:
upon a determination that the one or more images meet the threshold, providing a proceed indication to proceed to a next imaging sequence.

16. A non-transitory, computer-readable medium storing instructions executable by circuitry of an imaging system, the instructions comprising:
instructions to evaluate a diagnostic utility of one or more images of an imaging sequence acquired by the imaging system based on a combination of a diagnostic purpose and a specified reviewer; and
instruction to provide a re-scan indication upon a determination that the one or more images do not meet a threshold established for the combination of the diagnostic purpose and the specified reviewer;
wherein the instruction to evaluate the diagnostic utility of one or more images further comprises:
instructions to determine a probability of each of a plurality of images being good in an imaging volume;
instructions to determine an arithmetic mean or a geometric mean of the probabilities for the plurality of images; and
instructions to compare the arithmetic mean or the geometric mean with the threshold.

17. The non-transitory, computer-readable medium of claim 16, wherein the instruction to evaluate the one or more images comprise a rule-based algorithm or a trained deep-learning network.

18. The non-transitory, computer-readable medium of claim 16, wherein the diagnostic purpose corresponds to a disease state or an anatomical or physiological condition for which the patient is being evaluated.

19. The non-transitory, computer-readable medium of claim 16, wherein the instructions further comprise:
instructions to receive an input comprising a scan order or the scan order and at least a portion of an electronic medical record;
instructions to automatically determine an imaging protocol comprising at least the imaging sequence in response to the input.

20. The non-transitory, computer-readable medium of claim 16, wherein the instructions further comprise:
instructions to provide an alternative imaging protocol for performing the image acquisition upon the determination that the one or more images do not meet the threshold established for the combination of the diagnostic purpose and the specified reviewer.

* * * * *